United States Patent [19]

Stroppolo et al.

[11] Patent Number: 6,005,005
[45] Date of Patent: Dec. 21, 1999

[54] LIQUID PHARMACEUTICAL COMPOSITION FOR ORAL USE CONTAINING 2-(4-ISOBUTYLPHENYL) PROPIONIC ACID

[75] Inventors: Federico Stroppolo, Pregassona, Switzerland; Daniele Bonadeo, Varese, Italy; Luigi Vigano', Taverne, Switzerland; Annibale Gazzaniga, deceased, late of Rescaldina, Italy, by Cisella Adele Marabelli Gazzaniga, Giovanni Battista Gazzaniga, legal representatives; by Paola Maria Gazzaniga, legal representative, Busto Arsizio, Italy

[73] Assignee: Zambon Group S.p.A., Vicenza, Italy

[21] Appl. No.: 08/553,549

[22] PCT Filed: Jun. 15, 1994

[86] PCT No.: PCT/EP94/01944

§ 371 Date: May 6, 1996

§ 102(e) Date: May 6, 1996

[87] PCT Pub. No.: WO95/00134

PCT Pub. Date: Jan. 5, 1995

[30] Foreign Application Priority Data

Jun. 21, 1993 [IT] Italy .................... MI93A1326

[51] Int. Cl.⁶ .................... A61K 31/195; A61K 31/19
[52] U.S. Cl. ............................. 514/565; 514/570
[58] Field of Search ...................... 514/565, 570

[56] References Cited

U.S. PATENT DOCUMENTS

| | | |
|---|---|---|
| 3,271,314 | 9/1966 | Ecke et al. . |
| 4,689,218 | 8/1987 | Gazzaniga et al. ............... 424/43 |
| 4,861,797 | 8/1989 | Haas .................................. 514/557 |
| 5,175,376 | 12/1992 | Nieminen et al. . |
| 5,500,226 | 3/1996 | Stroppolo et al. ............... 424/466 |

OTHER PUBLICATIONS

International Search Report, dated Jan. 12, 1996, for International Application No. PCT/EP.95/03676.

Journal of the American Chemical Society, vol. 79, No. 18, Sep. 24, 1957, Washington, D.C., pp. 5019,5023.

Journal of Organic Chemistry, vol. 41, No. 26, Dec.24, 1976, Washington, D.C. pages L. R. Subramanian, et al, "On attempts at solvolytic generation of aryl cations," compound 9, p. 4100.

T. H. Coffield et al, "Some reductions of 2,6–dialkylphenols," (1980) J. of Org. Chem. vol. 41, No. 26, p. 5023.

*Primary Examiner*—Raymond Henley, III
*Attorney, Agent, or Firm*—Nikaido Marmelstein Murray & Oram, LLP

[57] ABSTRACT

A liquid pharmaceutical composition for oral use containing 2-(4-isobutylphenyl)-propionic acid, as the active ingredient, and arginine is described.

5 Claims, No Drawings

LIQUID PHARMACEUTICAL COMPOSITION FOR ORAL USE CONTAINING 2-(4-ISOBUTYLPHENYL) PROPIONIC ACID

The present invention relates to a liquid pharmaceutical composition for oral administration containing 2-(4-isobutylphenyl) propionic acid as the active ingredient, and more particularly, it relate to a liquid pharmaceutical composition containing 2-(4-isobutylphenyl)propionic acid and arginine.

2-(4-isobutylphenyl)propionic acid, hereinafter designated as "Ibuprofen," is a known non-steroidal antiinflammatory drug (Merck Index XI ed., n.4812, page 476) used in therapy for its analgesic, anti-pyretic and anti-inflammatory activity.

Notwithstanding Ibuprofen's use in therapy for years in its racemic form, (RS)-Ibuprofen, it has been known for some time that the enantiomer with the (S) configuration, (S)-lbuprofen, is the active eriantiomer.

Nevertheless, (R)-Ibuprofen aids in the pharmacological activity of the racemate since it is partially transformed into the (S) enantiomer by the organism. For a bibliographic reference on this subject, see, for example, S. S. Adams et al., J. Pharm. Pharmac., 28, 256–257, (1976).

For simplicity, hereinafter the term Ibuprofen will indicate the (S) form as well as the racemic form.

Liquid injectable formulations containing Ibuprofen and basic amino acids in equimolar amounts are known.

U.S. Pat. No. 4,279,926 (SPA - SocietàProdotti Antibiotici S.p.A.) describes injectable liquid formulations containing (RS)-Ibuprofen lysinate. U.S. Pat. No. 4,877,620 (Medice Chem. Pharm. Fabrik Putter GmbH & Co. KG) describes injectable liquid formulations containing a mixture 1:1 of (S)-lbuprofen and lysine.

There are also known solid formulations containing Ibuprofen and a molar excess of basic amino acids which can be used to prepare extemporaneous aqueous solutions.

U.S. Pat. No. 4,689,218 (Zambon S.p.A.) describes an effervescent composition consisting of Ibuprofen 9–17% by weight, arginine 17–33% by weight, sodium or potassium bicarbonate 20–35% by weight, sodium bitartrate 25–40% by weight.

U.S. Pat. No. 4,834,966 (Zambon S.p.A.) describes a pharmaceutical composition consisting of Ibuprofen 33–46% by weight, arginine 34–51% by weight, sodium bicarbonate 9–29% by weight.

However, the formulations containing Ibuprofen and basic amino acids described in the literature are not suitable for the preparation of liquid pharmaceutical forms for oral use such as concentrated aqueous solutions diluted in water at the moment of the administration. In fact, liquid pharmaceutical forms for oral use such as, for example, oral drops, must be chemically and physically stable for a long time even after a first use.

We have now found a liquid pharmaceutical composition for oral use consisting of an aqueous solution of a mixture of arginine and Ibuprofen, in a molar ratio between 1.1 and 1.5, so that the weight/volume concentration of Ibuprofen is equal to or greater than 200 mg/ml, and of optional excipients.

Preferably, L-arginine is used in the compositions of the present invention. More preferably, arginine is used in a molar ratio 1.1 with respect to Ibuprofen.

The excipients optionally present in the pharmaceutical composition of the present invention are the usual excipients suitable for the preparation of liquid pharmaceutical forms for oral use to be diluted at the moment of use, such as sweetening agents, flavoring agents and preservatives.

The liquid pharmaceutical compositions of the present invention are characterized by a remarkable chemical and physical stability.

The stability tests show the absence of precipitation or degradation phenomena assuring a constant titer of the active ingredient for at least 3 years. In particular, the liquid compositions of the present invention have been shown to be stable (i.e., with a practically constant titer of the active ingredient) after 1 year at 50° C., 40° C., 30° C. and room temperature. This is particularly worth noting in the case of highly concentrated aqueous solutions.

Furthermore, the pharmaceutical compositions of the present invention are characterized by a remarkable efficacy and by a rapid onset of the pharmacological effect; thus, they are particularly suitable for analgesic therapy.

From a practical point of view, the liquid pharmaceutical compositions of the present invention will be distributed in 10–50 ml bottles containing from 2 g to 20 g of Ibuprofen.

The dosage will be administered at from 10 to 40 drops, to be diluted in water at the moment of use, corresponding to a single dose of Ibuprofen between 100 mg and 400 mg.

In order to illustrate the present invention without limiting it, the following examples are now given.

EXAMPLE 1

L-arginine (185 g) and then (S)-lbuprofen (200 g) were added to boiling water (1000 ml) to obtain a limpid solution. Sodium saccharine (15 g) was added. After cooling, apricot flavor (50 g) and cetylpyridinium chloride (0.1 g) were added and the solution was poured into 30 ml holding bottles.

The solution (1 ml corresponding to about 20 drops) had the following composition:

(S)-lbuprofen 200 mg

L-arginine 185 mg

Sodium saccharine 15 mg

Apricot flavor 50 mg

Cetylpyridinium chloride 0.1 mg

Distilled water q.s. to 1 ml.

EXAMPLE 2

By working in a way similar to that described in Example 1, a solution having the following composition was prepared:

(RS)-Ibuprofen 200 mg

L-arginine 185 mg

Sodium saccharine 15 mg

Apricot flavor 50 mg

Methylparaben 1.8 mg

Propylparaben 0.2 mg

Distilled water q.s. to 1 ml.

EXAMPLE 3

L-arginine (185 g) and then (S)-Ibuprofen (200 g) were added to boiling water (1000 ml) to obtain a limpid solution. Sodium saccharine (15 g) was added. After cooling, apricot flavor (50 g) and ethanol (200 mg) were added and the solution was poured into 30 ml bottles.

The solution (1 ml corresponding to about 20 drops) had the following composition:

(S)-Ibuprofen 200 mg
L-arginine 185 mg
Sodium saccharine 15 mg
Apricot flavor 50 mg
Ethanol 200 mg
Distilled water q.s. to 1 ml.

The stability of the above composition after 1 year at 50° C., 40° C., 30° C. and at room temperature is reported in Table A below.

The titer of the (S)-Ibuprofen was expressed as a percentage relative to the starting concentration (100%).

TABLE A

Titer (%) of (S)-Ibuprofen after storage for 1 year at 50° C., 40° C., 30° C. and room temperature (R.T.)

| Temperature | (S)-Ibuprofen (%) after 1 year |
|---|---|
| 50° C. | 100.1 |
| 40° C. | 100.5 |
| 30° C. | 100.7 |
| R.T. | 100.9 |

The (S)-Ibuprofen value remained virtually unchanged, as did the pH value.

EXAMPLE 4

By working in a way similar to that described in Example 3, a solution having the following composition was prepared:

(RS)-Ibuprofen 200 mg
L-arginine 185 mg
Sodium saccharine 15 mg
Apricot flavor 50 mg
Ethanol 200 mg
Distilled water q.s. to 1 ml.

The stability of the above composition after 1 year at 50° C., 40° C., 30° C. and at room temperature is reported in Table B.

TABLE B

The titer of (RS)-Ibuprofen is expressed as a percentage of the starting concentration (100%).

| Temperature | (S)-Ibuprofen (%) after 1 year |
|---|---|
| 50° C. | 99.0 |
| 40° C. | 100.0 |
| 30° C. | 98.6 |
| R.T. | 100.0 |

The (RS)-Ibuprofen value remained virtually unchanged, as did the pH value.

EXAMPLE 5

L-arginine (185 g) and then (S)-Ibuprofen (200 g) were added to boiling water (1000 ml) obtaining a limpid solution. After cooling, sodium bicarbonate (40 g), sodium saccharine (15 g) and apricot flavor (50 g) were added and the solution was distributed into 30 ml holding bottles.

The solution has the following composition (1 ml volume corresponding to about 20 drops):

(S) - Ibuprofen 200 mg
L-arginine 185 mg
Sodium saccharine 15 mg
Sodium bicarbonate 40 mg
Apricot flavor 50 mg
Distilled water q.s to 1 ml.

The stability data of the above composition after 1 year at 50° C., 40° C., 30° C., and room temperature are reported in the following Table C.

TABLE C

The titer of (S)-Ibuprofen was expressed as a percentage with respect to the starting concentration (100%).

| Temperature | (RS)-Ibuprofen (%) after 1 year |
|---|---|
| 50° C. | 100.8 |
| 40° C. | 100.4 |
| 30° C. | 100.1 |
| R.T. | 100.9 |

The pH value remained practically unchanged.

EXAMPLE 6

By working in a manner similar to that described in Example 5, a solution having the following composition was prepared:

(RS)-Ibuprofen 200 mg
L-arginine 185 mg
Sodium saccharine 15 mg
Sodium bicarbonate 40 mg
Apricot flavor 50 mg
Distilled water q.s. to 1 ml.

The stability data of the above composition after 1 year at 50° C., 40° C., 30° C. and room
temperature are reported in the following table D.

The titer of (RS)-Ibuprofen was expressed as a percentage (%) with respect to the starting concentration (100%).

TABLE D

| Temperature | (RS)-Ibuprofen (%) after 1 year |
|---|---|
| 50° C. | 98.6 |
| 40° C. | 98.6 |
| 30° C. | 99.5 |
| R.T. | 99.8 |

The pH value too remained practically unchanged.

We claim:

1. A liquid pharmaceutical composition for oral use consisting of an aqueous solution of a mixture of arginine and Ibuprofen, in a molar ratio between 1.1 and 1.5, so that the weight/volume concentration of Ibuprofen is equal to or higher than 200 mg/ml, and of optional excipients.

2. A pharmaceutical composition according to claim 1 wherein Ibuprofen is (RS)-Ibuprofen.

3. A pharmaceutical composition according to claim 1 wherein Ibuprofen is (S)-Ibuprofen.

4. A pharmaceutical composition according to claim 1 wherein arginine is L-arginine.

5. A pharmaceutical composition according to claim 1 wherein the molar ratio is 1.1.

* * * * *